United States Patent [19]
Ahlquist et al.

[11] Patent Number: 5,846,795
[45] Date of Patent: *Dec. 8, 1998

[54] RNA TRANSFORMATION VECTOR

[75] Inventors: Paul G. Ahlquist; Roy C. French, both of Madison, Wis.

[73] Assignee: Mycogen Plant Science, Inc., San Diego, Calif.

[ * ] Notice: The term of this patent shall not extend beyond the expiration date of Pat. No. 5,500,360.

[21] Appl. No.: 462,714

[22] Filed: Jun. 5, 1995

Related U.S. Application Data

[63] Continuation of Ser. No. 212,330, Mar. 14, 1994, Pat. No. 5,500,360, which is a continuation of Ser. No. 916,799, Jul. 17, 1992, abandoned, which is a continuation of Ser. No. 368,939, Jun. 19, 1989, abandoned, which is a continuation of Ser. No. 709,181, Mar. 7, 1985, abandoned.

[51] Int. Cl.$^6$ .............................. C12N 15/33; C12N 5/10; C12N 15/82; C07H 21/02
[52] U.S. Cl. .................................... 435/172.3; 435/320.1; 435/419; 536/23.72; 536/24.1; 536/24.5
[58] Field of Search .............................. 536/23.72, 24.1, 536/24.5; 435/69.1, 70.1, 172.3, 235.1, 320.1, 948, 240.4, 240.2, 419

[56] References Cited

U.S. PATENT DOCUMENTS 5,500,360   3/1996   Ahlquist et al. ..................... 435/172.3

OTHER PUBLICATIONS

Franssen. H. (1984) Embo J. 3:855.
Hasseloff, J. et al. (1984) Proc. Natl. Acad. Sci. USA 81:4358.
Ahlquist, P. et al. (1985) J. Virol. 53:536.
Ahlquist, P. et al. (1981) J. Mol. Biol. 153:23.
Ahlquist, P. et al. (1984) J. Mol. Biol. 172:369.
Ahlquist, P. and Janda, M. (1984) Mol. Cell Biol. 4:2876.
Siegel, A. (1985) Plant Mol. Biol. 4:327–329.
Van Vloten–Doting et al. (1985) Plant Mol. Biol. 4:323–326.
French, R. and Ahlquist, P. (1987) J. Virol. 61:1457–1465.
Ahlquist, P. et al. (1987) Adv. Virus Res. 32:215–242.
Ahlquist, P. and French, R. (1988) in RNA GEnetics Book 2: RNA Variability, Domingo et al. (eds.), CRC Press, Orlando, Florida.
Strauss et al. 1994. Microbiological Reviews 58: 491–562.

*Primary Examiner*—David Guzo
*Attorney, Agent, or Firm*—Saliwanchik, Lloyd & Saliwanchik

[57] ABSTRACT

A +strand RNA viral transformation of host organisms with foreign RNA, and expression of said foreign RNA. The foreign RNA is inserted into an infective RNA viral segment containing replication elements, and allowed to infect the host organism. The invention is exemplified utiliing brome mosaic RNA modified to contain a gene coding for chloramphenicol acetyl transferase (CAT) in the transformation of barley protoplasts.

30 Claims, 6 Drawing Sheets

RNA TRANSFORMATION VECTOR

This is a continuation of application Ser. No. 08/212,330, filed Mar. 14, 1994, now U.S. Pat. No. 5,500,360; which is a continuation of Ser. No. 07/916,799, filed Jul. 17, 1992, now abandoned; which is a continuation of Ser. No. 07/368,939, filed Jun. 19, 1989, now abandoned; which is a continuation of Ser. No. 06/709,181, filed Mar. 7, 1985, now abandoned.

FIELD OF THE INVENTION

This invention relates to the field of plant viruses, more particularly to (+) strand RNA viruses of plants animals and bacteria, and to modifications, made according to the teachings herein, which permit insertion of an exogenous RNA segment into the viral genome. The inserted segment can then be introduced into a host cell in order to modify the cell, either genotypically or phenotypically. The invention is exemplified by modifications of an RNA plant virus, brome mosaic virus (BMV), which is infective for monocots.

BACKGROUND AND PRIOR ART

RNA viruses whose genome is composed of a single RNA strand capable of replication in the cytoplasm of a host by direct RNA replication are wide-spread, many varieties of which are known and which infect animals, plants and bacteria. Such viruses are sometimes termed "(+) strand RNA viruses" since the infective RNA strand, that normally found encapsidated in the virus particle, is a messenger-sense strand, capable of being directly translated, and also capable of being replicated under the proper conditions by a direct process of RNA replication. Viruses belonging to this group include, but are not limited to, the picornaviruses, the RNA bacteriophages, the comoviruses, and various single component and multicomponent RNA viruses of plants. A partial listing of such viruses would include polio virus, sindbis virus, Qβ bacteriophage, tobacco mosaic virus, barley stripe mosaic virus, cow pea mosaic virus, cucumber mosaic virus, alfalfa mosaic virus and brome mosaic virus. In some cases, the entire virus genome is contained within a single RNA molecule, while in other cases, most notably the multicomponent RNA plant viruses, the total genome of the virus consists of two or more distinct RNA segments, each separately encapsidated. (For general review, see *General Virology*, S. Luria and J. Darnell; *Plant Virology* 2nd ed., R. E. F. Matthews, Academic Press (1981); and for a general review of (+) strand RNA replication, see Davies and Hull (1982) J. Gen. Virol. 61,1). Within the group there are wide variations in capsid morphology, coat proteins, genetic organization genome size.

Despite the well-documented diversity, recent studies have shown striking similarities between the proteins which function in RNA replication. Sequence homologies have been reported between the cowpea mosaic virus, poliovirus and foot-and-mouth disease virus (Franssen, H. (1984) EMBO Journal 3,855), between non-structural proteins encoded by alfalfa mosaic virus, brome mosaic virus and tobacco mosaic virus, Haseloff, J. et al. (1984), Proc. Nat. Acad. Sci. USA 81, 4358, and between the same proteins and proteins encoded by sindbis virus, Ahlquist, P. et al. (1985) J. Virol. 53, 536. Evidence of such substantial homology in proteins related to the replication functions indicate that the viruses share mechanistic similarities in their replication strategies and may actually be evolutionarily related. In the present invention, modifications to the genomic RNA of a (+) strand RNA virus are disclosed. The modified RNA is used to transfer a desired RNA segment into a targeted host cell and to replicate that segment and express its function within the host cell. A virus known to be representative of the common replication functions of (+) strand RNA viruses was chosen to exemplify the present invention herein.

Brome mosaic virus (BMV) is one member of a class of plant viruses characterized by a multipartite RNA genome. The genetic material of the virus is RNA, and the total genetic information required for replication and productive infection is divided into more than one discrete RNA molecule. The class, termed multipartite RNA viruses herein, includes, besides BMV, such viruses as alfalfa mosaic virus (AMV), barley stripe mosaic virus, cowpea mosaic virus, cucumber mosaic virus, and many others. Virus particles are generally composed of RNA encapsidated by a protein coat. The separate RNA molecules which comprise the total genome of a given multipartite virus are encapsidated in separate virus particles, each of which has the same protein composition. Infection of a host plant cell occurs when a virus particle containing each of the RNA components of the viral genome has infected the cell, for example by exposing a plant to a virus preparation containing a mixture of all necessary viral components. Infection may also be achieved by exposing a plant cell or protoplast to a mixture of the RNA components. A subclass of the multipartite RNA viruses (termed subclass I herein) requires coat protein in addition to viral RNA for replication and productive infection. AMV is an example of a subclass I multipartite virus. Another subclass (termed subclass II herein) does not require coat protein, the component RNAs being both necessary and sufficient for replication and productive infection. BMV belongs to subclass II. The BMV genome is divided among three messenger-sense RNAs of 3.2, 2.8 and 2.1 kilobases (Ahlquist, P. et al. (1981) J. Mol. Biol. 153,23; Ahlquist, P., et al. (1984) J. Mol. Biol. 172,369). The term "messenger-sense" denotes that the viral RNAs can be directly translated to yield viral proteins, without the need for an intervening transcription step.

Complete cDNA copies of each of the three BMV genetic components have been cloned in a general transcription vector, pPM1, described by Ahlquist, P. and Janda, M. (1984) Mol. Cell Biol. 4,2976. Three plasmids have been selected, pB1PM18, pB2PM25 and pB3PM1 containing, respectively, cDNA copies of BMV-RNA1, BMV-RNA2 and BMV-RNA3. The three plasmids constitute, as a set, the complete BMV genome.

DNA from each of the three BMV cDNA-containing plasmids can be cleaved at a unique EcoRI site. The linear DNA thus produced can be transcribed in vitro in a reaction catalyzed by RNA polymerase. A modified λ $P_R$ promoter in the transcription vector, pPM1, allows RNA synthesis to initiate exactly at the 5' terminus of each BMV sequence, and transcription continues to the end of the DNA template, adding 6–7 nonviral nucleotides at the 3' ends of the transcripts. When transcription is carried out in the presence of a synthetic cap structure, $m^7GpppG$, as described by Contreras, R., et al. (1982) Nucleic Acids Res. 10,6353, RNA transcripts are produced with the same capped 5' ends as authentic BMV RNA's. These RNAs are active messengers in in vitro translation systems and direct production of proteins with the same electrophoretic mobilities as those translated from authentic BMV RNAS.

SUMMARY OF THE INVENTION

For the sake of brevity, the term "RNA virus" is used herein to mean (+) strand replicating RNA viruses.

The invention is based on the discovery that an RNA of the genome of an RNA virus can be modified to include an exogenous RNA segment and that the modified RNA can be introduced into a host cell, replicated therein and can express the exogenous RNA segment. The recipient cell is thereby phenotypically transformed and may contribute to a genotypically transformed organism, as well. Phenotypically transformed cells can be modified in vivo, in planta, in tissue culture, in cell culture or in the form of protoplasts. The exemplified embodiment of the invention is useful for producing phenotypically transformed plants under field conditions or greenhouse growth. Traits desirable for introduction in this manner include, but are not limited to, pest resistance, pathogen resistance, herbicide tolerance or resistance, modified growth habit and modified metabolic characteristics, such as the production of commercially useful peptides or pharmaceuticals in plants. The modifications can be applied at any time during the growth cycle, depending on the need for the trait. For example, resistance to a pest could be conferred only if the crop were at risk for that pest, and at the time when the crop was most likely to be affected by the pest. Other traits can be used to enhance secondary properties, for example to increase the protein content of post-harvest forage. Any plant variety susceptible to infection by a multipartite RNA virus can be phenotypically transformed. The choice of virus and the details of modification will be matters of choice depending on parameters known and understood by those of ordinary skill in the art. Other uses for cells and organisms phenotypically or genotypically modified by means of a modified RNA derived from an RNA virus will be readily apparent to those skilled in the art, given a wide range of RNA viruses to modify and a wide range of susceptible host cell types. Other uses for transformed animal cells, bacterial cells and the like can be readily envisioned. For example, bacterial cells susceptible to Qβ phage can be grown in culture to desired cell density, infected with a modified Qβ phage carrying a desired gene and thereby caused to express large quantities of a desired protein within a short time period.

Generally, the steps of a process for phenotypically transforming a cell or organism are: forming a full-length cDNA transcript of the virus RNA, or of each RNA component if the RNA virus is multipartite; cloning each cDNA in a transcription vector; modifying the cDNA of at least one of the RNA components by inserting a non-viral DNA segment in a region able to tolerate such insertion without disrupting RNA replication thereof; transcribing the modified cDNA, or, in the case of a multipartite virus, transcribing each cDNA corresponding to an RNA component of the multipartite virus; substituting the modified cDNA for its unmodified counterpart in the transcription reaction; infecting virus-susceptible protoplasts, cells, tissues or whole organisms with transcribed RNA, or a mixture of RNAs, either in solution or encapsidated, of each viral component including the modified RNA comprising messenger-sense RNA containing an exogenous RNA segment. From this point, the steps to be followed will vary, depending on the type of material infected and the route of infection. Protoplasts, cells and tissues of plants can be propagated vegetatively, regenerated to yield whole plants by means of any technique suitable to the particular plant variety infected, and transplanted to the field. Whole plants can be infected in situ. Infected plants and plant cells can produce many copies per cell of the modified viral RNA containing the exogenous RNA segment. If desired and if suitably inserted, by means of principles and processes known in the art, the exogenous RNA segment can be caused to carry out a function within the cell. Such a function could be a coding function, translated within the cell to yield a desired peptide or protein, or it could be a regulatory function, increasing, decreasing, turning on or off the expression of certain genes within the cell. Any function which a segment of RNA is capable of providing can, in principle, be expressed within the cell. The exogenous RNA segment thus expressed confers a new phenotypic trait to the transformed organism, plant, cells, protoplasts or tissues.

The invention is exemplified herein by the modification of BMV RNA to contain a structural gene encoding chloramphenicol acetyl transferase (CAT) and the phenotypic modification of barley protoplasts therewith, yielding protoplasts synthesizing CAT. The data presented herein are believed to represent the first instance of phenotypic modification of a cell by means of a modified RNA of an RNA virus.

DETAILED DESCRIPTION OF THE INVENTION

Figure 1:
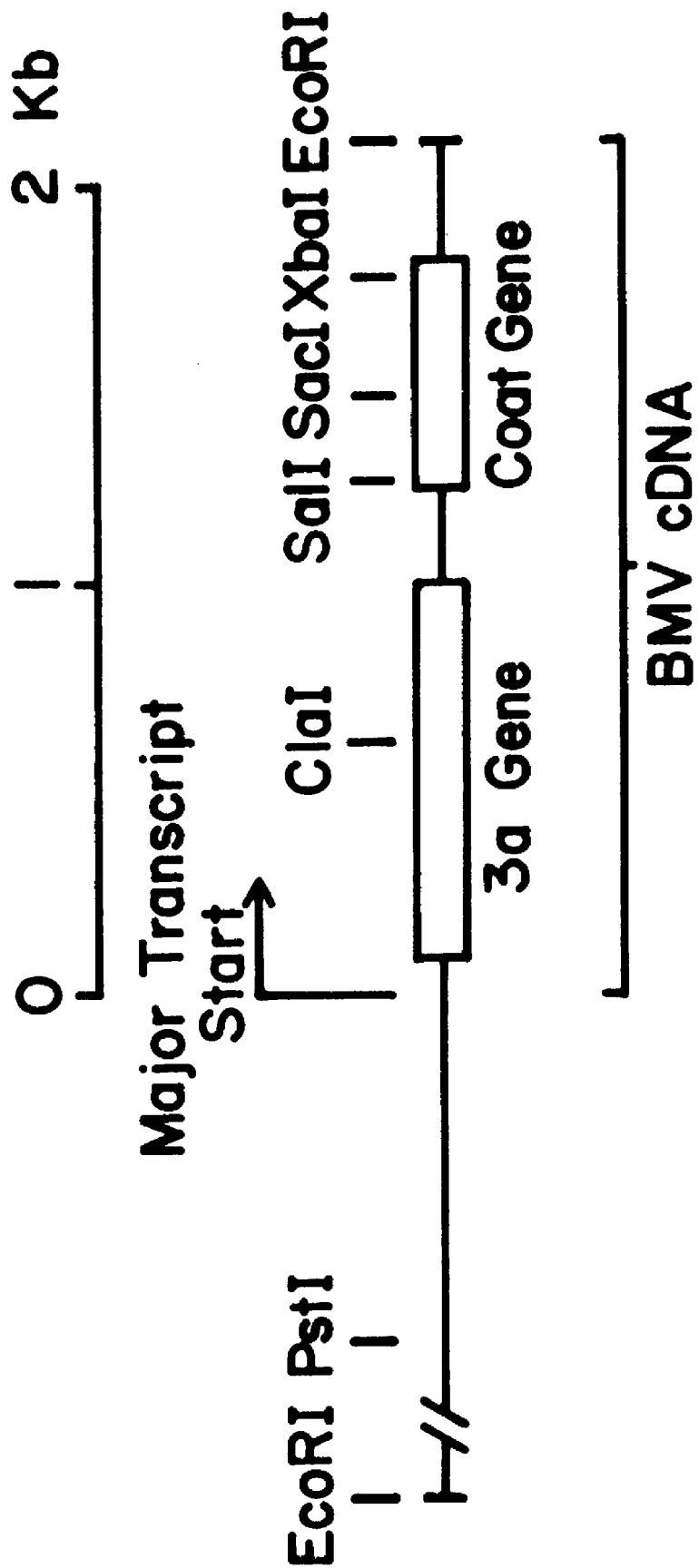
FIG. 1 shows a map of EcoRI-cleaved pB3M1.

In order to facilitate understanding of the invention, certain terms used throughout are herein defined.

RNA virus—The term as used herein means a virus whose genome is RNA in single-stranded form, the single strand being a (+) strand, or messenger-sense strand. Replication of the viral (+) strand in a virus-infected cell occurs by a process of direct RNA replication and is therefore distinguishable from the replication mechanism of retroviruses which undergo an intermediate step of reverse transcription in the host cell.

Cis-acting replication element—This term denotes that portion of the RNA genome of an RNA virus which must be present in cis, that is, present as part of each viral strand as a necessary condition for replication. Virus replication presumably depends upon the existence of one or more trans (diffusible) elements which interact with the cis-acting element to carry out RNA replication. While trans-acting elements are necessary for replication, they need not be present or coded for on the modified RNA provided they are made available within the infected cell by some other means. For example, in the case of a mulitpartite RNA virus, the trans-acting functions may be provided by other, unmodified components of the viral genome used to transform the cells simultaneously with the modified RNA. The target cell may also be modified in a previous step to provide constitutive expression of the trans-acting functions. The cis-acting replication element is composed of one or more segments of viral RNA which must be present on any RNA molecule that is to be replicated within a host cell by RNA replication. The segment will most likely be the 5' terminal portion of the viral RNA molecule, and may include other portions as well. The cis-acting element is therefore defined in functional terms: any modification which destroys the ability of the RNA to replicate in a cell known to contain the requisite trans-acting elements, is deemed to be a modification in the cis-acting replication element. Conversely, any modification, such as an insertion in a sequence region which is able to tolerate such insertion without disrupting replication, is a modification outside the cis-acting replication element. As is demonstrated herein, using the example of BMV, substantial portions of an RNA virus molecule may be modified, by deletion, insertion, or by a combination of deletion and insertion, without disrupting replication.

The term "derived from" is used to identify the viral source of an RNA segment which comprises part of the modified RNA. For example, for the modified RNAs described herein, substantial portions thereof are derived from BMV. The manner of deriving, whether by direct recombination at the RNA level, by transcription or by reverse transcription does not matter for the purpose of the invention. Indeed, it is contemplated that modifications may be made within the cis-acting replication element and elsewhere for example to modify the rate or amount of replication that is obtained. In the case of modified RNAs exemplified herein, a transcription vector was employed which preserved the exact 5' terminal nucleotide sequence of viral RNA. However the use of such a vector in transcribing viral RNA from cDNA is not considered essential to the invention, although it will be preferred if preservation of the exact nucleotide sequence at the 5' end is desired. An RNA segment which has been derived from a given source virus may, but need not be, identical in sequence to that segment as-it exists in the virus. It will be understood that a cis-acting replicating element derived from a given RNA virus may have minor modifications in the nucleotide sequence thereof without substantially interfering with RNA replication.

Exogenous RNA segment is a term used to describe a segment of RNA to be inserted into the virus RNA to be modified, the source of the exogenous RNA segment being different from the RNA virus itself. The source may be another virus, a living organism such as a plant, animal, bacteria, virus or-fungus; the exogenous RNA may be a chemically synthesized RNA or it may be a combination of the foregoing. The exogenous RNA segment may provide any function which is appropriate and known to be provided by an RNA segment. Such functions include, but are not limited to, a coding function in which the RNA acts as a messenger RNA encoding a sequence which, translated by the host cell, results in synthesis of a peptide or protein having useful or desired properties; the RNA segment may also be structural, as for example in ribosomal RNA, it may be regulatory, as for example with small nuclear RNA's or anti-sense RNA, or it may be catalytic. A particularly interesting function is provided by antisense RNA, sometimes termed (−) strand RNA, which is in fact a sequence complementary to another RNA sequence present in the target cell which can, through complementary base pairing, bind to and inhibit the function of the RNA in the target cell.

Various aspects of the stages outlined in the Summary section can be modified as needed, depending upon specific aspects of the virus selected as the transforming agent and of the RNA segment to be inserted. For example, if the inserted gene is in the form of messenger-sense RNA to be directly translated by the transformed cell, the gene must be free of intervening, nontranslated sequences, such as introns. On the other hand, the inserted gene need not be a naturally occurring gene, but may be modified, a composite of more than one coding segment, or it may encode more than one protein. The RNA may also be modified by combining insertions and deletions in order to control the total length or other properties of the modified RNA molecule. As demonstrated in Example 5, a substantial portion of the RNA3 of BMV can be deleted without significantly effecting its replication in cells containing normal RNA1 and RNA2. The inserted non-viral gene may be either prokaryotic or eukaryotic in origin as long as it is in a form which can be directly translated by the translation machinery of the recipient cell. Eukaryotic genes containing introns within the coding sequence must therefore be inserted in the form of a cDNA copy of the eukaryotic messenger RNA encoding the gene. The inserted gene may contain its own translation start signals, for example, a ribosomal binding site and start (AUG) codon, or it may be inserted in a manner which takes advantage of one or more of these components preexisting in the viral RNA to be modified. Certain structural constraints must be observed to preserve correct translation of the inserted sequence, according to principles well understood in the art. For example, if it is intended that the exogenous coding segment is to be combined with an endogenous coding segment, the coding sequence to be inserted must be inserted in reading frame phase therewith and in the same translational direction. The term "non-viral" is used herein in a special sense to include any RNA segment which is not normally contained within the virus whose modification is exploited for effecting gene transfer and is therefore used synonymously with "exogenous". Therefore, a gene derived from a different virus species than that modified is included within the meaning of the terms "non-viral" and "exogenous" for the purposes of describing the invention. For example, a non-viral gene as the term is used herein could include a gene derived from a bacterial virus, an animal virus, or a plant virus of a type distinguishable from the virus modified to effect transformation. In addition, a non-viral gene may be a structural gene derived from any prokaryotic or eukaryotic organism. It will be understood by those ordinarily skilled in the art that there may exist certain genes whose transfer does not result in obvious phenotypic modification of the recipient cell. Such may occur, for example, if the translation product of the nonviral gene is toxic to the host cell, is degraded or processed in a matter which renders it non-functional or possesses structural features which render it impossible for the host cell to translate in sufficient quantities to confer a detectable phenotype on the transformed cells. However, the invention does not depend upon any specific property of an RNA segment or gene being transferred. Therefore, the possible existence of RNA segments or genes which fail to confer a readily observable phenotypic trait on recipient cells or plants is irrelevant to the invention and in any case will be readily recognizable by those of ordinary skill in the art without undue experimentation.

An exogenous RNA segment may be inserted at any convenient insertion site in any of the cDNA sequences corresponding to a viral RNA, or component RNA of a multipartite RNA virus, provided the insertion does not disrupt a sequence essential for replication of the RNA within the host cell. For example, for a virus whose coat protein is not essential for replication, an exogenous RNA segment may be inserted within or substituted for the region which normally codes for coat protein. As desired, regions which contribute to undesirable host cell responses may be deleted or inactivated, provided such changes do not adversely effect the ability of the RNA to be replicated in the host cell. For many single component and multipartite RNA viruses, a reduction in the rate of normal RNA replication is tolerable and will in some instances be preferred, since the amount of RNA produced in a normal infection is more than enough to saturate the ribosomes of the transformed cell.

The transformation process itself can be carried out by any means whereby RNA can be introduced into cells, whole plants, plant tissues or protoplasts. Host cells can be infected by the RNA alone, or encapsidated in a virus particle, except that the modified viral RNA containing a non-viral RNA segment is substituted for its counterpart in a normal infection. Any other suitable means for introducing RNA into target cells such as microinjection may be used. In some cases it may be preferable to include all of the normal components in addition to the modified component. More than one component may be modified in the mixture of transforming components. It will be understood that the amounts of each infecting component must be sufficient to insure that an adequate number of cells receive at least one of each component in the mixture. Other variables of the infection process, such as pretreatment of the recipients, addition of components to enhance the efficiency of infection, use of encapsidated or unencapsidated RNA, are matters of choice which those of ordinary skill in the art will be able to manipulate to achieve desired transformation efficiency in a given situation. For instance, the choice of multipartite plant RNA virus to be modified to effect gene transfer in a given plant variety will depend upon known host range properties of multipartite RNA viruses. For example, BMV infects a variety of grasses and their related domesticated relatives including barley, wheat and maize. Plant cells which are infected in culture will normally remain transformed as the cells grow and divide since the RNA components are able to replicate and thus become distributed to daughter cells upon cell division. Plants regenerated from phenotypically modified cells, tissues or protoplasts remain phenotypically modified. Similarly, plants transformed as seedlings remain transformed during growth. Timing of application of the transforming components will be governed by the result which is intended and by variations in susceptibility to the transforming components during various stages of plant growth.

Many plant RNA viruses are seed transmitted from one generation to the next. This property can be exploited to effect genotypic transformation of a plant. That is to say, the modified RNA remains transmissible from one generation to the next, most likely by replication in the cytoplasm, and thereby becomes transmissible from one generation to the next, just as seed-borne virus infections are transmitted from one generation to the next.

The following examples illustrate the principles of the invention as applied to modification of BMV RNA3 and the use of modified BMV RNA3 containing a gene coding for chloramphenicol acetyl transferase (CAT) in the phenotypic transformation of barley protoplasts. For convenience, any modification to a viral RNA which includes the insertion of a nonviral ribonucleotide sequence, whether or not combined with a deletion of viral RNA will be designated by a prime symbol following the number designating the RNA. For example, modified RNA3 is termed RNA3', or more generally, RNAn is designated RNAn'.

The following examples utilize many techniques well known and accessible to those skilled in the arts of molecular biology, cloning, plant cell biology, plant virology and plant tissue culture. Such methods are fully described in one or more of the cited references if not described in detail herein. Unless specified otherwise, enzymes were obtained from commercial sources and were used according to the vendor's recommendations or other variations known to the art. Reagents, buffers and culture conditions and reaction conditions for various enzyme catalyzed reactions are also known to those in the art. Reference works containing such standard techniques include the following: R. Wu, ed. (1979) Meth. Enzymol. 68; R. Wu et al., eds. (1983) Meth. Enzymol. 100, 101; L. Grossman and K. Moldave, eds. (1980) Meth. Enzymol. 65; J. H. Miller (1972) *Experiments in Molecular Genetics*; R. Davis et al. (1980) *Advanced Bacterial Genetics*; R. F. Schleif and P. C. Wensink (1982) *Practical Methods in Molecular Biology*; and T. Manniatis et al. (1982) *Molecular Cloning*.

Textual use of the name of a restriction endonuclease in isolation, e.g., "BclI" refers to use of that enzyme in an enzymatic digestion, except in a diagram where it can refer to the site of a sequence susceptible to action of that enzyme, e.g., a restriction site. In the text, restriction sites are indicated by the additional use of the word "site", e.g., "BclI site". The additional use of the word "fragment", e.g., "BclI fragment", indicates a linear double-stranded DNA molecule having ends generated by action of the named enzyme (e.g., a restriction fragment). A phrase such as "BclI/SmaI fragment" indicates that the restriction fragment was generated by the action of two different enzymes, here BclI and SmaI, the two ends resulting from the action of different enzymes. Note that the ends will have the characteristics of being either sticky (i.e., having a single strand of protrusion capable of base-pairing with a complementary single-stranded oligonucleotide) or blunt (i.e., having no single-stranded protrusion) and that the specificity of a sticky end will be determined by the sequence of nucleotides comprising the single-stranded protrusion which in turn is determined by the specificity of the enzyme which produces it.

All plasmids are designated by a sequence of letters and numbers prefaced by a lower case "p", for example, pPM1. Clones of complete BMV cDNA inserted in pPM1 are named by the format pBxPMy, where x equals 1, 2 or 3 designating the BMV component cloned (i.e., from RNA1, 2 or 3) and y is an arbitrary isolate number. Thus, the set of three plasmids, pB1PM18, pB2PM25 and pB3PM1 contains complete cDNA copies of BMV RNAs 1, 2 and 3, respectively, and represent, as a set, the complete BMV genome. Certain steps of cloning, selection and vector increase employed strains of *E. coli*. While the strains used herein have been designated, there are many equivalent strains available to the public which may be employed. The use of a particular microorganism as a substitute for a strain designated herein is a matter of routine choice available to those of ordinary skill in the art, according to well-known principles.

EXAMPLE 1

Infectivity of transcribed BMV-cDNA

In vitro Transcription. Transcription reactions contained 25 mM Tris-HCl, pH 8.0/5 mM $MgCl_2$/150 mM NaCl/1 mM dithiothreitol/200 $\mu$M each rATP, rCTP, and rUTP/25 $\mu$M rGTP/500 $\mu$M $m_7$GpppG (P-L Biochemicals)/plasmid DNA (0.1 $\mu$g/$\mu$l) *Escherichia coli* RNA polymerase (0.05 units/$\mu$l) (Promega Biotec, Madison, Wis.). Reactions were incubated 30 minutes at 37° C., by which time the GTP was nearly exhausted. Additional rGTP was added to 25 $\mu$M and incubation continued a further 30 minutes. For uncapped transcripts, $m^7$GpppG was deleted, GTP was increased to 200 $\mu$M, the concentrations of DNA and polymerase were doubled, and incubation was carried out for 1 hour. Reactions were stopped by addition of EDTA to 10 mM and either diluted directly in inoculation buffer or phenol-extracted before nucleic acid recovery by ethanol precipitation. In most experiments, plasmids representing all three BMV components were pooled and cleaved at unique EcoRI sites 3 base pairs past the 3' terminus of each BMV sequence before transcription. FIG. 1 shows a map of EcoRI-cleaved pB3M1. The maps for pPM1 containing cDNA of RNA1 or RNA2 are the same, except that the region labeled "BMV-cDNA" is cDNA of RNA-1 or RNA-2.

Infectivity Testing. Seven-day-old barley seedlings (*Hordeum vulgare* L. cv. Morex) were dusted with carborundum powder and inoculated with either virion RNA or in vitro transcription mixes in 50 mM Tris $PO_4$, pH 8.0/250 mM NaCl/5 mM EDTA/Bentonite (5 mg/ml) (5); 15–30 plants in a single 14-cm-diameter pot were treated with the same inoculum, using 10–30 µl per plant. Plants were scored for the presence of mosaic symptoms 7–14 days after inoculation.

BMV Isolation. Fourteen days after inoculation, virus was isolated from barley plants as described by Shih, et al. (1972) J. Mol. Biol. 64,353, with the substitution of chloroform for carbon tetrachloride and a second polyethylene glycol precipitation for differential centrifugation. Viral RNA was isolated by phenol extraction and ethanol precipitation.

Infectivity Testing of BMV cDNA Clones and Their in vitro Transcripts. Cloning of complete cDNA copies of all three BMV genetic components in a general transcription vector, pPM1, has been described by Ahlquist, P. and Janda, M. (1984) Mol. Cell. Biol. 4,2876. DNA from such clones can be cleaved with EcoRI (FIG. 1) and transcribed in vitro in the presence of a synthetic cap structure to produce complete RNA copies of the BMV components that have the same capped 5' ends as authentic BMV RNA's, and an additional 6–7 non-viral nucleotides at their 3' ends.

To test the infectivity of these cloned DNAs and their transcripts, three plasmids, pB1PM18, pB2PM25, and pB3PM1, were selected. The selected clones contain cDNA copies of BMV RNAs 1, 2, and 3, respectively, and represent, as a set, the complete BMV genome. The natural isolate of BMV propagated in our laboratory is referred to by its usual designation of Russian strain. Mixtures of the EcoRI-cut M1 plasmids and their capped transcription products were inoculated onto barley plants in parallel with untranscribed DNA from the same plasmids. As judged by the production of normal viral symptoms, the transcribed plasmid mixture was infectious, while the untranscribed plasmid mixture was not (Table 1).

TABLE 1

Comparison of infectivity of EcoRI-cut M1 plasmids; transcribed EcoR1-cut M1 plasmids, and Russian strain BMV virion RNA's over a range of inoculum concentrations.

| Pot No. | Inoculum, ng/µl | Plants with symptoms/total |
|---|---|---|
| | EcoRI-cut pB1PM18, pB2PM25; pB3PM1 | |
| 1 | 100 | 0/21 |
| 2 | 10 | 0/23 |
| 3 | 1 | 0/22 |

TABLE 1-continued

Comparison of infectivity of EcoRI-cut M1 plasmids; transcribed EcoR1-cut M1 plasmids, and Russian strain BMV virion RNA's over a range of inoculum concentrations.

| Pot No. | Inoculum, ng/µl | Plants with symptoms/total |
|---|---|---|
| | Transcribed EcoRI-cut pB1PM18, pB2PM25, pB3PM1 | |
| 4 | 40 | 19/23 |
| 5 | 4 | 7/20 |
| 6 | 0.4 | 0/21 |
| | Russian strain BMV virion RNA | |
| 7 | 10 | 21/22 |
| 8 | 1 | 14/21 |
| 9 | 0.1 | 2/21 |
| | Mock-inoculated | |
| 10 | 0 | 0/22 |

In vitro transcription yields approximately 3 BMV transcripts per plasmid (Ahlquist and Janda, 1984). Total BMV transcript content of the inocula for pots 4–6 is thus approximately 75, 7.5, and 0.75 ng/µl, respectively.

The effects of various alterations to the transcription protocol were examined to more clearly characterize the infectious entity observed in plasmid transcription mixes. Infectivity required transcription of clones representing all three BMV genetic components. Moreover, infectivity was sensitive to HinfI before or to RNase A after transcription, but it was not significantly affected by RNase A before or HinfI after transcription. HinfI cleaves at 8 sites within pPM1 and at 15, 10, and 12 sites within BMV 1, 2, and 3 cDNAs, respectively. These results confirm that the observed infectivity arises from the in vitro transcripts rather than directly from their DNA templates. In addition, when plasmids were either not cut or were cut with PstI before transcription (cleaving 2.7 kilobases rather than 7 bases downstream of the cDNA end), infection was not observed, suggesting that infectivity is affected by the structure of the transcript 3' end. Finally, if the cap analog was omitted during in vitro transcription, no infection was detected, even if inoculum concentration was increased 20-fold.

Infectivity of RNA transcribed in vitro from EcoRI-cut M1 plasmids was clearly lower than that of authentic BMV RNA. The number of infected plants produced from a given weight of in vitro-transcribed RNA was similar to that produced from 1/10th that weight of authentic BMV RNA (Table 1). The presence of the plasmid DNA template in the inoculum was not responsible for this effect, as addition of the same plasmid DNA to authentic BMV RNA did not affect its infectivity.

Correlation of Symptomology with BMV Replication. To establish that such symptoms accurately reflect BMV replication, several molecular tests were applied. Nitrocellulose dot blots of total RNA (described by Garger, S. J. et al. (1983) Plant Mol. Biol. Reporter 1,21) extracted from leaves of symptomexpressing and symptomless plants inoculated with either authentic BMV RNA or in vitro BMV transcripts were probed with $^{32}$P-labeled cloned BMV cDNA. In all cases, symptom-expressing leaves showed a positive hybridization response, and in all cases but one, symptomless leaves gave a negative response. The one exception was from a plant that had been inoculated with in vitro transcripts and showed no visible symptoms but gave a positive hybridization signal.

Virus isolated from plants infected with cDNA transcripts is serologically identical to Russian strain BMV in double-diffusion tests with anti-BMV antisera. Phenol extraction of BMV isolated from transcript-infected plants releases four RNAs that comigrate with Russian strain virion RNAs, hybridize to BMV-specific DNA probes, and are highly infectious in subsequent inoculations. Therefore, multipartite RNA plant virus infection can be derived solely from appropriately cloned viral cDNA by means of a simple transcription step.

EXAMPLE 2

Construction and replication of a specific deletion in the BMV coat gene

In the following example, reference may be made to FIG. 1 for location of the relevant restriction sites.

Plasmid pB3PM1 DNA (Ahlquist, P. and Janda, M. (1984)) was cleaved with SalI and XbaI and treated with the Klenow fragment of DNA polymerase I to generate blunt ends (Maniatis et al. (1982) *Molecular Cloning: A Laboratory Manual*. Cold Spring Harbor). The approximately 5.2 kb fragment was isolated from a low melting point (LMP) agarose gel (Sanger et al. (1980) J. Mol. Biol. 143,161), recircularized by treatment with T4 DNA ligase, and transformed into competent *E. coli* JM101. RF DNA from selected ampicillin resistant transformants was digested simultaneously with SalI and EcoRI to confirm regeneration of the SalI site and deletion of the desired fragment. A single tested clone, designated pB3DCP10, having the region of the coat gene from SalI to SbaI deleted, was selected for further work.

EcoRI-digested pB3DCP10 was transcribed under capping conditions (Ahlquist and Janda, 1984) along with EcoRI-digested pB1PM18 and pB2PM25 (Ahlquist and Janda, 1984), and the transcripts were separated from the plasmid DNA templates by LiCl precipitation (Baltimore (1966) J. Mol. Biol. 18, 421). Barley protoplasts were prepared as described by Loesch-Fries and Hall (1980) J. Gen. Virol. 47, 323. and inoculated as described by Samac et al. (1983) Virology 131, 455, with the transcripts and incubated in the presence of [$^3$H]uridine. Total nucleic acids were extracted and analyzed on acrylamide-agarose gels as described by Loesch-Fries and Hall, 1980. The deleted RNA3 derived from pB3DCP10 was found to both replicate and generate a deleted version of subgenomic RNA4. (RNA4 is a subgenomic fragment of RNA3 produced during infection). This example demonstrates that a substantial portion of RNA3 encoding coat protein can be deleted, without preventing replication of viral RNA's.

EXAMPLE 3

Insertion of a PstI site at the 3' cDNA end of plasmid pB3PM1

Figure 2:
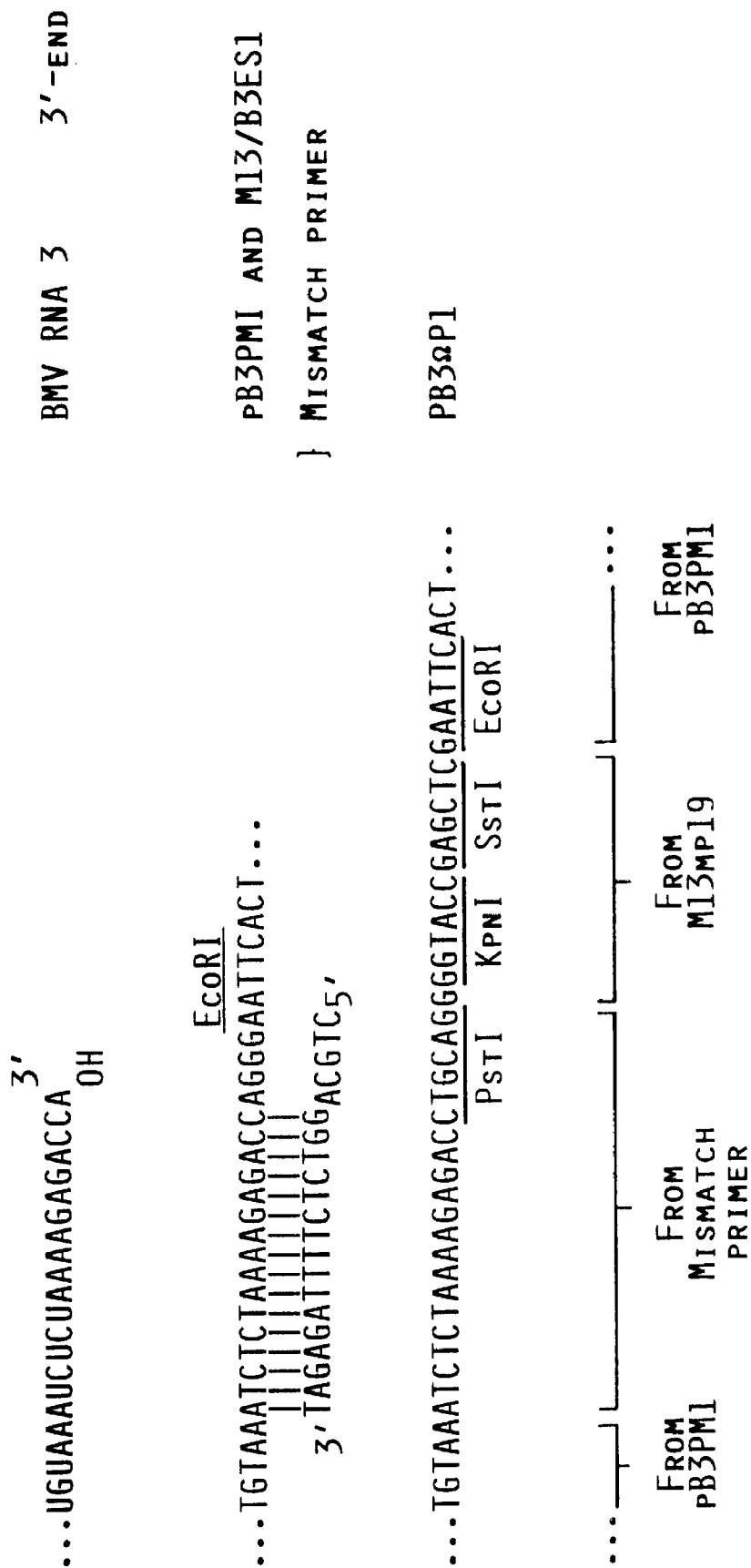
FIG. 2 shows a 21 nucleotide mismateh primer used to prime synthesis of DNA from M13/B3ES1.

Construction and use of transcribable BMV cDNA clones has been described before (Ahlquist et al., 1984a, 1984b). To define the transcript 3' end, the originally described plasmids are first linearized before transcription by cleavage of an EcoRI site just outside the 3' end of BMV cDNA. However, such EcoRI cleavage results in addition of 6–7 nonviral nucleotides to the transcript and is inconvenient for transcription of BMV-linked foreign sequences which contain EcoRI site(s). To deal with both of these problems, a PstI site, i.e., a nucleotide sequence including a sequence recognized and cleaved by PstI endonuclease, was inserted immediately adjacent to the BMV cDNA in pB3PM2 to provide an alternate cleavage site. The steps in the construction can be followed by referring to FIG. 2. DNA sequences shown in FIG. 2 are plus (+) strands only, defined as equivalent (not complementary) to the RNA sequence of BMV-RNA.

Insertion of this PstI site was generally similar to the previously described insertion of a SmaI site adjacent to the lambda $P_R$ promoter (Ahlquist and Janda, 1984). First the 0.9 kb SalI-EcoRI fragment of pB3PM1 (FIG. 1) was isolated from a low-melting point agarose gel and subcloned into SalI EcoRI cleaved M13mp9. Colorless recombinant plaques were selected on X-gal/IPTG plates and the insertion of BMV sequences verified by dideoxynucleotide sequencing (Biggen et al. (1983) Proc. Nat. Acad. Sci. USA 80, 3963). A single clone, designated M13/B3ES1, was selected for further work. A 21 nucleotide mismatch primer (FIG. 2) was chemically synthesized and purified and used to prime synthesis of $^{32}$P-labeled DNA from M13/B3ES1 ssDNA. After synthesis, the DNA was cleaved with AvaI at a site in the M13 vector distal to the primer and the major labelled DNA fragment, containing the mismatch primer at its 5' end and BMV3 sequences interior, was purified on an alkaline agarose low melting point gel (Maniatis et al., 1982). A second strand of DNA was primed with a lac reverse primer (Ahlquist and Janda, 1984), the ds synthetic DNA cleaved with XbaI and the approximately 0.36 kb dsDNA fragment, containing the mismatch primer linked to 3' BMV RNA3 sequences, isolated from a low melting point agarose gel. This fragment was then subcloned into XbaI-SmaI cut M13mp19. Colorless recombinant plaques were selected on X-gal/IPTG plates and the correct linkage of the PstI site to BMV cDNA confirmed by dideoxy sequencing. The 0.36 kb XbaI EcoRI fragment from a selected M13 clone was recloned between the XbaI and SalI sites of Pb3PM1, creating plasmid pB3ΩP1. The sequence of RNA transcribed from PstI-cleaved pB3ΩP1 will be identical to that of BMV RNA3 except that the 3'-terminal A will be omitted.

EXAMPLE 4

Figure 3:
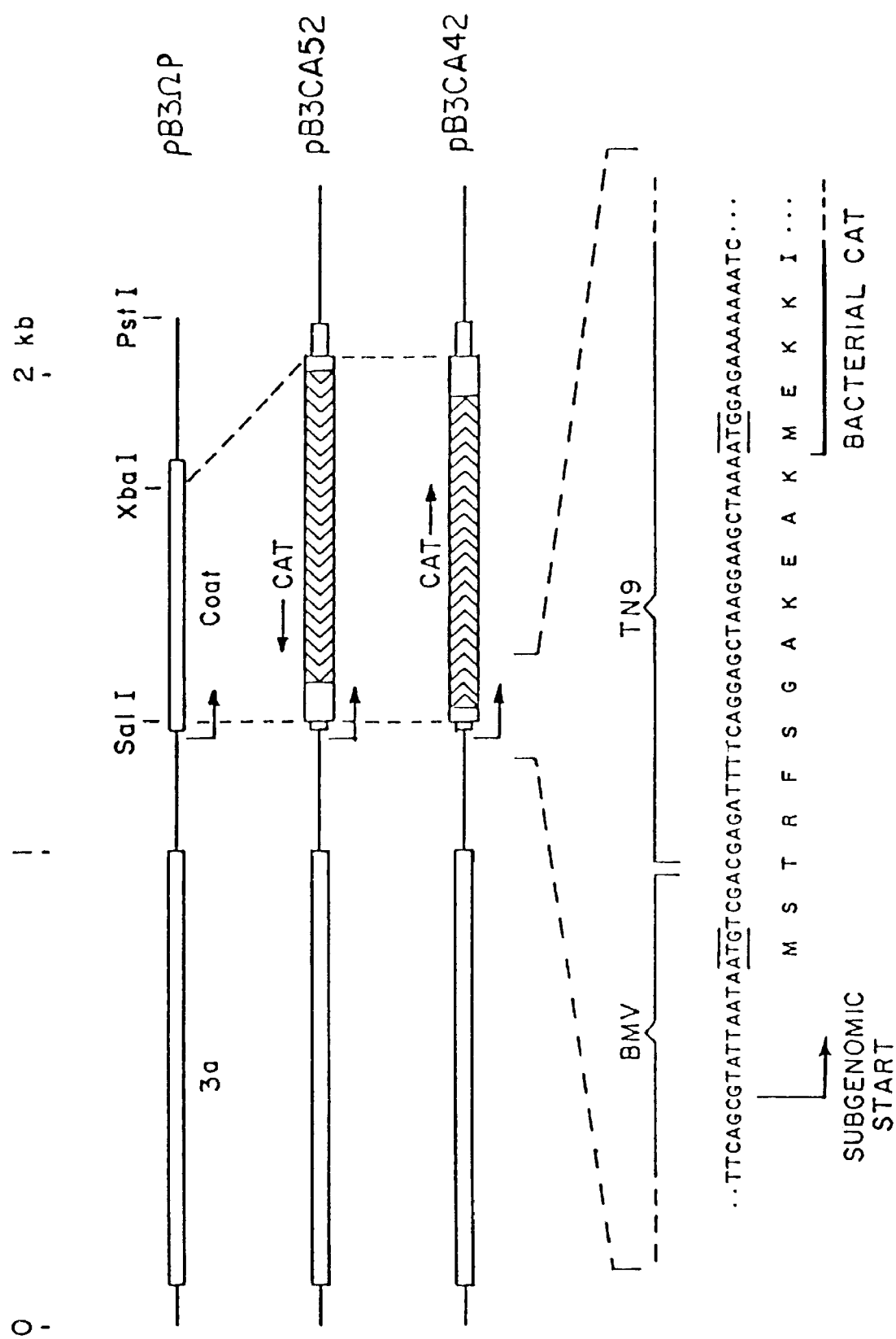
FIG. 3 shows the insertion of the CAT gene in in-frame linkage with the initiation codon of th BMV coat protein gene.

Insertion of a bacterial chloramphenicol resistance gene in a BMV RNA3 derivative and expression of a functional protein in barley cells Plasmid pB3ΩP1 (Example 3) was cleaved with SalI and XbaI to delete most of the coat protein gene except for seven nucleotides at the beginning of the coat protein coding sequence including the AUG start codon, treated with the Klenow fragment of DNA polymerase I to produce blunt ends and the resulting larger DNA fragment isolated from a low melting point agarose gel. Plasmid pBR325 (Bolivar, 1978) was digested with TaqI, treated with Klenow polymerase and the 780 bp fragment containing the chloramphenicol acyl transferase (CAT) gene was isolated. The 780 bp fragment isolated in this manner contained the entire CAT gene together with a short segment of pBR325 flanking the 5' end of the CAT gene coding sequence. The larger pB3ΩP1 fragment and a three-fold molar excess of the CAT fragment were ligated with T4 DNA ligase and transformed into *E. coli* JM101 cells. Plasmid DNA from selected ampicillin-resistant transformants was screened by double digestion with EcoRI and PstI and gel electrophoresis to confirm insertion of the CAT gene and to determine its orientation with respect to BMV3 cDNA sequences. One plasmid, pB3CA42, containing the CAT gene coding sequences in the same orientation as the BMV3 coding sequences was selected for further work along with a plasmid, pB3CA52, with the CAT gene in the reverse orientation. Insertion of the CAT gene in the positive orientation, as in pB3CA42, results in in-frame linkage of the CAT coding sequences with the initiation codon of the BMV coat gene (FIG. 3). Translation from the coat AUG would result in production of a fusion protein bearing 12 additional amino acids before the start of the native CAT gene product.

Figure 4:
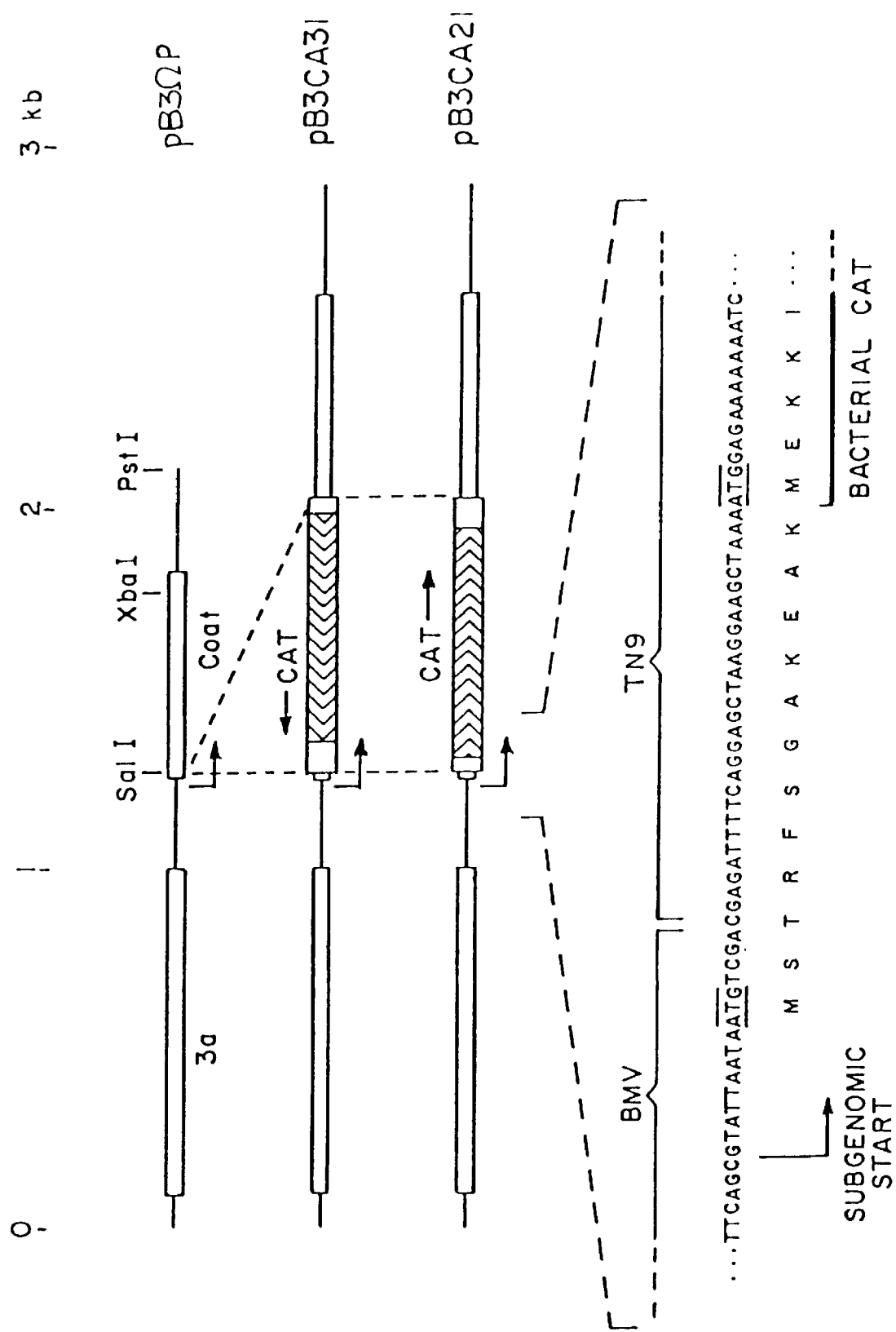
FIG. 4 shows the insertion of the CAT gene at the SalI site of pBΩP1.
Figure 5:
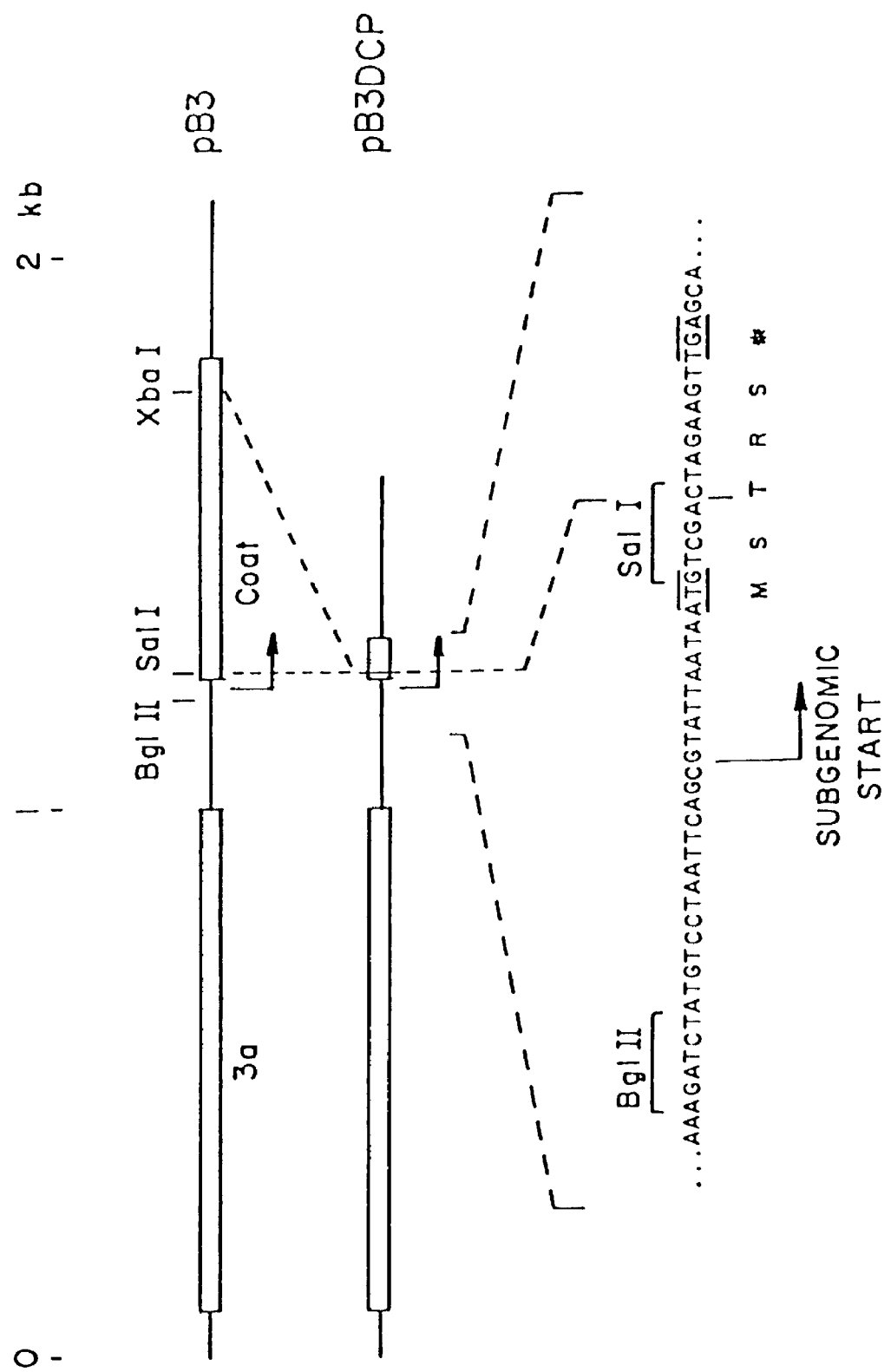
FIG. 5 shows file construction of pB3DCP.

In a similar construction, diagrammed in FIG. 4, the same CAT fragment was inserted at the SalI site of pB3Ω3 by SalI digestion followed by blunt ending with Klenow polymerase and ligation with DNA ligase. Two clones differing in the orientation of the CAT gene were isolated, pB3CA31 with the CAT gene coding sequence oriented backwards from the direction of transcription, and pB3CA21 with the CAT gene coding sequence oriented in the same direction as that of transcription. FIG. 4 also shows the nucleotide sequence in the region of the junction point between BMV-derived and bacterial-derived sequences, for pB3CA21. As a control, SalI/XbaI deleted pB3 without an insertion was constructed, designated pB3DCP, as shown in FIG. 5. The sequence in the region of the subgenomic transcription start site and religation site is also shown in FIG. 5. As a further control, the CAT coding sequence was deleted from plasmid pB3CA42 (FIG. 3) by cleaving with SalI, filling out the recessed 3' ends with Klenow DNA polymerase and deoxynucleotides, and religating the resultant blunt ends.

Figures 6A, 6B:
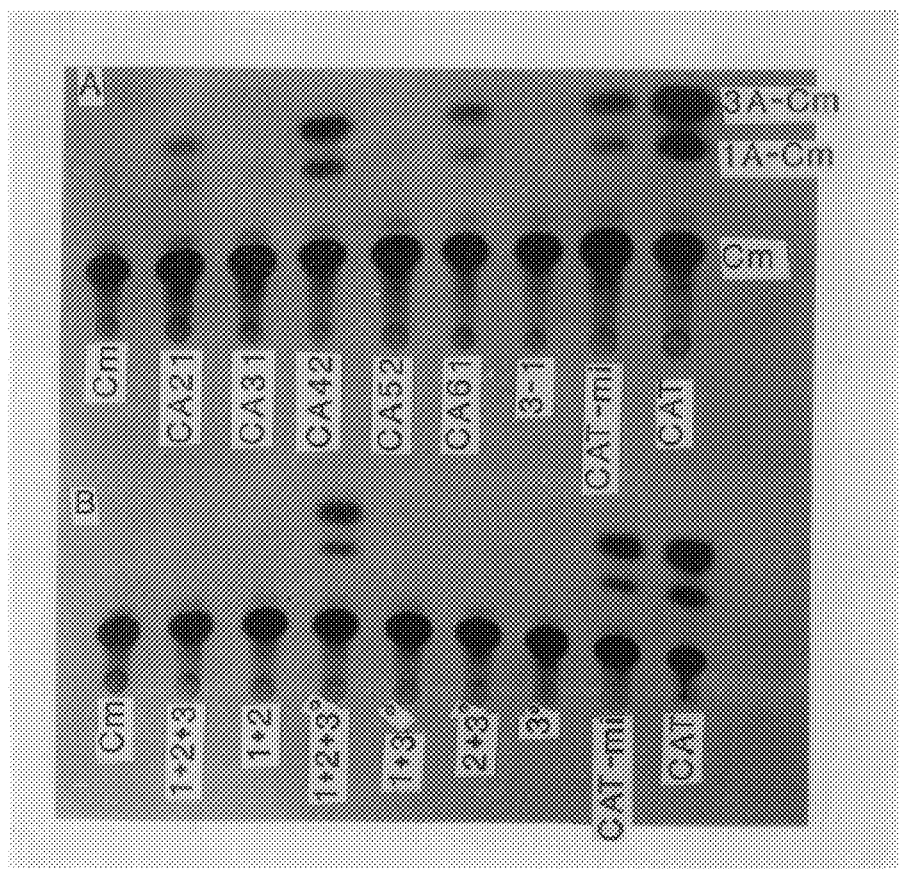
FIG. 6 (Parts a and b) shows the production of CAT by protoplasts inoculated with tanscripts constructed according to the invention.

PstI-cut pB3CA42 DNA and EcoRI-cut pB1PM18 and pB2PM25 DNAs were transcribed, LiCl-precipitated and used to inoculate protoplasts (Example 1). After 22 hours incubation protoplasts were lysed by freezing and thawing and were found to contain CAT activity as assayed by standard methods (Herrera-Estrella et al. (1983) Nature 303, 209; Shaw, (1975) Methods Enzymol. 53, 737). Cell lysates were incubated with [$^{14}$C] chloramphenicol and, following the published procedure, silica gel thin layer plates separating reactants and products were autoradiographed. The results are shown in FIG. 6. Lanes marked Cm were loaded with [$^{14}$C] chloramphenicol only. CAT activity in other reactions is indicated by the appearance of acetylated chloramphenicol forms marked 1A-Cm (1-acetate) and 3A-Cm (3-acetate) in addition to the native form marked Cm. The lanes marked CAT-mi and CAT show the products produced by authentic bacterial CAT in the presence of extracts from mock-inoculated protoplasts or buffer only. Panel A shows the products produced by extracts obtained from protoplasts inoculated with transcripts from pB1PM18 and pB2PM25, together with pB3CA21 (lane designated CA 21), pB3CA31 (lane designated CA 31), pB3CA42 (lane designated CA 42), pB3CA52 (lane designated CA 52), pB3CA61 (lane designated CA 61) or pB3PM1 (lane designated 3-1). In panel B the products obtained from extracts of protoplasts inoculated with various combinations of pB1PM18 (designated 1), pB2PM25 (designated 2); pB3PM1 (designated 3), and pB3CA42 (designated 3°) are shown. In parallel tests, mockinoculated protoplasts and protoplasts inoculated with transcripts from EcoRI-cut pB1PM18, EcoRI-cut pB2PM25 and either EcoRI-cut pB3PM1 or PstI-cut pB3CA52 showed no detectable CAT activity. The results shown in FIG. 6 demonstrate phenotypic transformation of the cells and further demonstrate that an RNA-3' containing an inserted nonviral coding segment, under appropriate conditions of infection, can effect such transformation. Only the combination of 1°+2°+3° provides expression of the CAT gene, showing that this expression is dependent on viral RNA replication.

EXAMPLE 5

Bal 31 Deletions in Plasmid pB3PM1

Plasmid pB3PM1 DNA was cleaved with ClaI, treated with T4 DNA polymerase to produce blunt ends, and ligated to phosphorylated 12 bp synthetic BamHI linkers (Maniatis et al., 1982). After phenol/chloroform extraction and ethanol precipitation, the DNA was cleaved with 40 units BamHI per µg linker for 16 hours at 37° C. After electrophoresis on 1% (w/v) low-melting point agarose the major ethidium bromide-staining band of DNA was eluted (Sanger et al., 1980) and recircularized by treatment with T4 DNA ligase at approximately 2 ng DNA/µl reaction, and transformed into competent E. coli JM101. RF DNA from randomly selected ampicillin-resistant transformants was digested simultaneously with BamHI and EcoRI and screened by gel electrophoresis to confirm the presence of the BamHI linker at the desired point. A single clone, designated pB3C49, was selected for further work.

12 µg of ClaI-cleaved pB3PM1 DNA was treated with 12 units of Bal 31 at room temperature in a 180 µl reaction (Guo et al. (1983) Nucleic Acids Res. 11, 2237). 30 µl aliquots were removed 2, 4, 6, 8, 10 and 12 minutes after enzyme addition. Nuclease digestion in each aliquot was terminated by addition of 25 µl of 40 mM EDTA and two successive phenol/chloroform extractions. The aliquots were pooled and the DNA precipitated with ethanol. The DNA was treated with the Klenow fragment of DNA polymerase I to generate blunt ends, and 12 bp synthetic BamHI linkers were added (Maniatis et al, 1982). After phenol/chloroform extraction and ethanol precipitation, the DNA was treated with 50 units BamHI/µg linker and 2 units PstI/µg plasmid for 16 hours at 37° C. Products were run on a low melting point agarose gel and the high MW fraction containing the approximately 4.2 kb ClaI/PstI fragment of pB3PM1 and its Bal 31-deleted, linker-ligated products was eluted and mixed with a molar excess of the approximately 1.5 kb PstI-BamHI fragment of pB3C49. After ligation, DNA was transformed into competent E. coli JM101 cells. RF DNA was prepared from randomly-selected ampicillin-resistant transformants and was screened by double digestion with BamHI and EcoRI followed by agarose gel electrophoresis. Plasmids with deletions extending a variety of distances from the initial ClaI site, within the 3a gene (FIG. 1), of pB3PM1 toward the EcoRI site were selected using this data. Selected plasmids were cleaved with EcoRI and transcribed (Example 1) and the transcripts used to infect barley protoplasts in the presence of transcripts from EcoRI-cut plasmids pB1PM18 and pB2PM25.

Using similar techniques a BamHI linker was inserted in the SacI site of pB3PM1 and two further Bal 31 deletion libraries were constructed, one with deletions extending 5' to the Sacd site and one with deletions 3' to the SacI site. Transcripts from selected EcoRI-cut plasmids were tested in the presence of transcripts from EcoRI-cut pB1PM18 and pB3PM25 in the barley protoplast system. Transcripts from pB3PM1 derivatives with linker insertions in either the ClaI and SacI sites, and from derivatives with deletions extending for up to several hundred bases from either site were found to replicate under such conditions. Substantial deletions within the 3a gene and the coat protein gene can therefore be made, at least several hundred bases from either the ClaI site of the SacI site, without preventing replication of the deleted RNA. Such deletions provide room for large insertions while still staying within the size constraints for packaging replicated RNA3' into virus particles. The remaining portion of RNA, derived from RNA3, contains a cis-acting replication element of BMV RNA. Although the 3A gene and coat gene were not required for RNA replication or for expression of the inserted CAT gene under the conditions of infection used in the example, either or both of these genes could, under other conditions, provide important secondary functions, for example, by promoting systemic infection during transfer of whole plants. Where deletion is not desired but the length of the modified RNA exceeds the packaging constraints of the icosahedral BMV capsid, it may be possible to provide for expression of the coat protein of a rod-shaped virus for encapsidating the modified RNA.

Discussion and Conclusions

The foregoing examples demonstrate that substantial modifications, both deletions and insertions, can be made in an RNA component of a multipartite RNA virus without preventing replication of viral RNA under appropriate conditions of infection. Genetic material inserted within a region of an RNA virus that is nonessential for RNA replication is translatable. In the case of BMV, substantial portions of RNA3 can be deleted without loss of the ability to replicate. Therefore any gene inserted within a nonessential region of an RNA component of an RNA multipartite virus can be translated in the transformed cell, provided the gene has appropriate ribosome binding and translation initiation signals at its 5' end. These signals can be provided by the virus or by the insert and the means for making translatable constructions is within the scope of capability of those ordinarily skilled in the art.

While the foregoing principles were illustrated in the case of BMV RNA3, it is apparent that any component of any RNA virus is a candidate for modifications of the type illustrated. For example, an exogenous RNA segment could be inserted at any site of BMV RNA 1 or 2 which does not result in loss of ability to replicate. Similarly, the RNA components of other RNA viruses can be similarly manipulated, provided the insertions and/or deletions employed do not prevent replication of viral RNA. The two operating principles which permit the modification of a viral RNA component to make it a vector for carrying translatable genetic material into a host cell are: (1) cloning a cDNA of the RNA component into a transcription vector capable of transcribing replicatable RNA from viral cDNA, and (2) the identification of a region in one of the viral components that is nonessential for replication, into which a structural gene can be inserted. The modified RNA will therefore contain, at a minimum, a cis-acting replication element derived from an RNA virus and an inserted exogenous RNA segment. Further modifications and improvements following and embodying the teachings and disclosures herein are deemed to be within the scope of the invention, as set forth in the appended claims.

We claim:

1. An RNA molecule comprising a cis-acting replication element derived from a (+) strand RNA plant virus capable of replication in a plant cell and further comprising an exogenous RNA segment capable of expressing its function in a host cell, said exogenous RNA segment being located in a region of said RNA molecule able to tolerate said segment without disrupting RNA replication of said RNA molecule in the presence of trans-acting replication elements in said host cell.

2. The RNA of claim 1, wherein the exogenous RNA segment codes for a peptide or protein.

3. The RNA of claim 1, wherein the exogenous RNA segment comprises antisense RNA.

4. The RNA of claim 1, wherein the exogenous RNA segment comprises structural RNA.

5. The RNA of claim 1, wherein the RNA segment comprises a regulatory RNA.

6. The RNA of claim 1, wherein the exogenous RNA segment comprises RNA having catalytic properties.

7. The RNA of claim 1, wherein the cis-acting replication element is derived from a multipartite plant virus.

8. The RNA of claim 1, wherein the cis-acting replication element is derived from tobacco mosaic virus.

9. The RNA of claim 1, wherein the cis-acting replication element is derived from alfalfa mosaic virus.

10. The RNA of claim 1, wherein the cis-acting replication element is derived from brome mosaic virus.

11. The RNA molecule of claim 1, encapsidated with a viral coat protein.

12. A DNA transcription vector comprising cDNA having one strand complementary to an RNA molecule comprising a cis-acting replication element derived from a (+) strand RNA plant virus capable of replication in a plant cell and further comprising an exogenous RNA segment capable of expressing its function in a host cell, said exogenous RNA segment being located in a region of said RNA molecule able to tolerate said segment without disrupting RNA replication of said RNA molecule in the presence of trans-acting replication elements in said host cell.

13. The DNA transcription vector of claim 12, wherein one strand of the cDNA thereof is complementary to RNA coding for a nonviral protein or peptide.

14. The DNA transcription vector of claim 12, wherein one strand of the cDNA thereof is complementary to RNA having a regulatory, structural, or catalytic property.

15. The DNA transcription vector of claim 12, wherein one strand of the cDNA thereof is complementary to an RNA segment derived from a multipartite plant virus.

16. The DNA transcription vector of claim 12, wherein one strand of the cDNA thereof is complementary to an RNA segment derived from a tobacco mosaic virus.

17. The DNA transcription vector of claim 12, wherein one strand of the cDNA thereof is complementary to an RNA segment derived from an alfalfa mosaic virus.

18. The DNA transcription vector of claim 12, wherein one strand of the cDNA thereof is complementary to an RNA segment derived from a brome mosaic virus.

19. A method of modifying a host cell, genotypically or phenotypically, which method comprises introducing into the cell an RNA molecule comprising a cis-acting replication element derived from a (+) strand RNA plant virus capable of replication in a plant cell and further comprising an exogenous RNA segment capable of expressing its function in a host cell, said exogenous RNA segment being located in a region of said RNA molecule able to tolerate said segment without disrupting RNA replication of said RNA molecule in the presence of transacting replication elements in said host cell, whereby the exogenous RNA segment confers a detectable trait in the host cell, thereby modifying said host cell.

20. The method of claim 19, wherein the exogenous RNA molecule codes for a peptide or protein.

21. The method of claim 19, wherein the exogenous RNA segment comprises antisense RNA.

22. The method of claim 19, wherein the exogenous RNA segment comprises structural RNA.

23. The method of claim 19, wherein the exogenous RNA segment comprises a regulatory RNA.

24. The method of claim 19, wherein the exogenous RNA segment comprises RNA having catalytic properties.

25. The method of claim 19, wherein the cis-acting replication element is derived from a multipartite plant virus.

26. The method of claim 19, wherein the cis-acting replication element is derived from tobacco mosaic virus.

27. The method of claim 19, wherein the cis-acting replication element is derived from alfalfa mosaic virus.

28. The method of claim 19, wherein the cis-acting replication element is derived from brome mosaic virus.

29. The method of claim 19, wherein the host cell is a plant cell.

30. The method of claim 19, wherein the host cell is a monocot plant cell.

* * * * *

UNITED STATES PATENT AND TRADEMARK OFFICE
CERTIFICATE OF CORRECTION

PATENT NO. : 5,846,795

DATED : December 8, 1998

INVENTOR(S) : Paul G. Ahlquist, Roy C. French

It is certified that error appears in the above-identified patent and that said Letters Patent is hereby corrected as shown below:

Column 2, line 36: "Ahiquist" should read --Ahlquist--.

Column 4, line 20: "mismateh" should read --mismatch--; and line 28: "file construction" should read --the construction--.

Column 5, line 46: "or-fungus;" should read --or fungus,--.

Column 8, line 60: "$m_7$GpppG" should read --$m^7$GpppG--;

line 63: "GTP" should read --rGTP--; and

Column 8, line 66: "GTP" should read --rGTP--.

Column 10, line 61: "symptomexpressing" should read --symptom-expressing--.

Column 13, line 55: "(designated 2);" should read --(designated 2),--; and line 57: "mockinoculated" should read --mock-inoculated--.

UNITED STATES PATENT AND TRADEMARK OFFICE
CERTIFICATE OF CORRECTION

PATENT NO. : 5,846,795
DATED : December 8, 1998
INVENTOR(S) : Paul G. Ahlquist, Roy C. French It is certified that error appears in the above-identified patent and that said Letters Patent is hereby corrected as shown below:

Column 14, line 53: "Sacd" should read --*SacI*--.

Column 16, line 51: "transacting" should read --trans-acting-- .

Signed and Sealed this

Thirtieth Day of March, 1999

Attest:

Q. TODD DICKINSON

*Attesting Officer*   *Acting Commissioner of Patents and Trademarks*